United States Patent [19]

Hall et al.

[11] 4,445,387

[45] May 1, 1984

[54] COMPRESSION SHEAR TEST JIG

[75] Inventors: Henry J. Hall, Arden Hills; John G. Haygreen, Roseville, both of Minn.

[73] Assignee: Regents of the University of Minnesota, Minneapolis, Minn.

[21] Appl. No.: 389,292

[22] Filed: Jun. 17, 1982

[51] Int. Cl.$^3$ .............................................. G01N 3/24
[52] U.S. Cl. ...................................... 73/845; 73/846
[58] Field of Search .................................. 73/845, 846

[56] References Cited

FOREIGN PATENT DOCUMENTS 629284 10/1978 U.S.S.R. ................................ 73/846

OTHER PUBLICATIONS

Gaudert, P. 1974, New Torsion Test for Particleboard, Forest Products Journal, 24(2):35–37.
Gertjejansen, R. and Haygreen, J. 1971, Torsion Shear Test for Particleboard Adapted to a Universal Testing Machine, Forest Products Journal, 21(11):59–60.
Heebink, B. and Gatchell, C. 1965, A Proposed Plug Tension Test for Particleboard, Forest Products Journal, 15(1):28–30.
Kufner, M. 1975, Die Prüfung der Bindefestigkeit von Spanplatten (Testing the Binding Strength of Particleboard), Holz als Roh–und Werkstoff, 33(1975):265–270.
Lehmann, W. 1965, Simplified Test of Internal Bond in Particleboard, Forest Products Journal, 15(5):223–224.
Liiri, O., Kivistö, A., Tuominen, M. and Aho, M. 1980, Determination of the Internal Bond of Particleboard and Fiberboard, Holz als Roh–und Werkstoff, 38(1980):185–193.
Shen, K. et al., 1969, Compression Shear Strength of Particleboard and its Relationship to Internal Bond, Department of Fisheries and Forestry, Canadian Forestry Service, F.P.L. Ottawa, Ontario, Information Report OP-X-22, 15 pp.
Shen, K. and Carroll, M. 1969, A New Method for Evaluation of Internal Strength of Particleboard, Forest Products Journal, 19(8):17–22.
Shen, K. 1970, Correlation Between Internal Bond and the Shear Strength Measured by Twisting Thin Plates of Particleboard, Forest Products Journal, 20(11):16–20.
Suchsland, O. 1977, Compression Shear Test for Determination of Internal Bond Strength in Particleboard, Forest Products Journal, 27(1):32–36.
Passialis, C. and Tsoumis, G. 1982, Method for Testing Internal Bond of Particleboard, Wood and Fiber, 14(2):159–161.

Primary Examiner—Howard A. Birmiel
Attorney, Agent, or Firm—Burd, Bartz & Gutenkauf

[57] ABSTRACT

A compression shear test jig for determining the internal shear strength of the weakest plane of a wood fiber or particle panel product. The test jig comprises an upper and lower loading head adapted to be used in conjunction with a universal testing machine or press. The upper and lower loading heads are each provided with a sample engaging face disposed at substantially a 45° angle. These faces are in parallel spaced apart relation. The bottom end of the lower face and top end of the upper face are each provided with a sample restraining element. The lower head body includes a base which rests upon a low friction surface permitting unrestrained lateral movement to occur as shear strain develops. Preferably the upper loading head includes a pivoted cap so that compressive force is applied uniformly. The sample engaging faces are preferably formed in separable face plates which are adjustable relative to the loading head bodies to compensate for samples of different thicknesses. The preferred low friction surface is formed by the upper edges of a plurality of parallel rollers. In use, a test specimen is placed between the opposed sample engaging faces and a measured compressive force is applied until the specimen shears.

16 Claims, 6 Drawing Figures

COMPRESSION SHEAR TEST JIG

BACKGROUND OF THE INVENTION

1. Field of the Invention

This invention is directed to a compression shear test jig, which is useful for determining the internal shear strength in the plane of a wood fiber or particle panel product. The principal object of the invention is to provide the wood fiberboard or particleboard producer, secondary manufacturer and researcher, a quick, simple and definitive means for determining the internal strength of these products so that internal bond and shear strength in the plane of the panel can be approximated. The jig is useful as a quality control tool for producers. Secondary manufacturers may use it to determine acceptability of shipments received. Research institutions find it useful for their research and developmental efforts.

2. The Prior Art

The standard test for determining the internal strength of wood fiberboard and particleboard is called the internal bond (IB) or tensile strength perpendicular to the surface test. It requires a specimen 2 in. square and of the thickness of the finished panel bonded on each face with suitable adhesive to 2 inch square loading blocks of steel, aluminum alloy or wood. A tensile load is applied at a uniform rate to the faces as nearly perpendicular as possible. The specimen is tested to failure in the weakest plane and the failing load is recorded.

Because fabrication of IB test specimens is time consuming and messy, there have been many attempts to devise alternative methods for approximating this property. However, each alternative has the disadvantage of either requiring gluing or not necessarily testing the specimen in the weakest plane.

Suchsland (Compression shear test for determination of internal bond strength in particleboard. Forest Products Journal 27(1): 32–36. 1977) discloses a test method based upon the basic engineering mechanics principle that an axial force develops maximum shear stress at an angle 45° to the direction of the force. However, gluing of a test specimen is required. The gluing requirement of Suchsland's technique probably is the reason why it has not gained acceptance by the particleboard industry. Specimens to be tested by Suchsland's technique are parallelogram in shape and have the width dimension limited to the thickness of the test specimen. These are viewed as disadvantages. Although the Suchsland method embodies the test principle that forms the basis for this invention, these disadvantages are avoided with this invention.

SUMMARY OF THE INVENTION

In its broadest terms, the compression shear test jig of the present invention comprises an upper and lower loading head adapted to be used in conjunction with a universal testing machine or press. The upper loading head includes a body having a bottom sample engaging face disposed at substantially a 45° angle. The face is preferably roughened to grip the specimen and transfer the shear force from the loading head to the test specimen. A sample restraining element is provided at the upper end of the gripping face.

The lower loading head includes a body immediately below the upper head. That body has a top sample engaging face disposed at substantially a 45° angle and spaced from and substantially parallel to the bottom face of the upper head for receiving a sample between the faces. This top sample engaging face is also preferably provided with a sample gripping surface and a sample restraining element at its lower end. The lower head body includes base plate which rests upon a low friction surface permitting unrestrained lateral movement to occur as shear strain develops.

Preferably, the upper loading head includes a pivoted cap so that compressive force is applied uniformly even if the sample thickness is somewhat uneven. The sample engaging faces are preferably formed in separable face plates which are adjustable relative to the loading head bodies to compensate for samples of different thicknesses. The preferred low friction surface is formed by the upper edges of the plurality of parallel rollers. Orientation of the system in use is variable. Accordingly, any references to upper, lower, top, bottom, vertical, etc. relate only to the orientation shown in the drawings.

BRIEF DESCRIPTION OF THE DRAWINGS

The invention is illustrated in the accompanying drawings in which corresponding parts are identified by the same numerals and in which.

DETAILED DESCRIPTION OF THE PREFERRED EMBODIMENT

Figure 1:
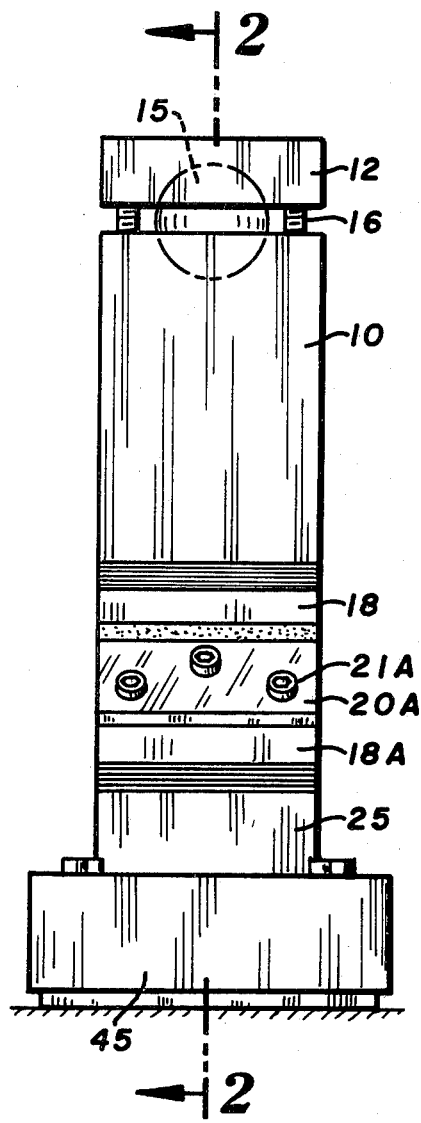
FIG. 1 is a left end elevation of the compression shear test jig of the present invention.
Figure 2:
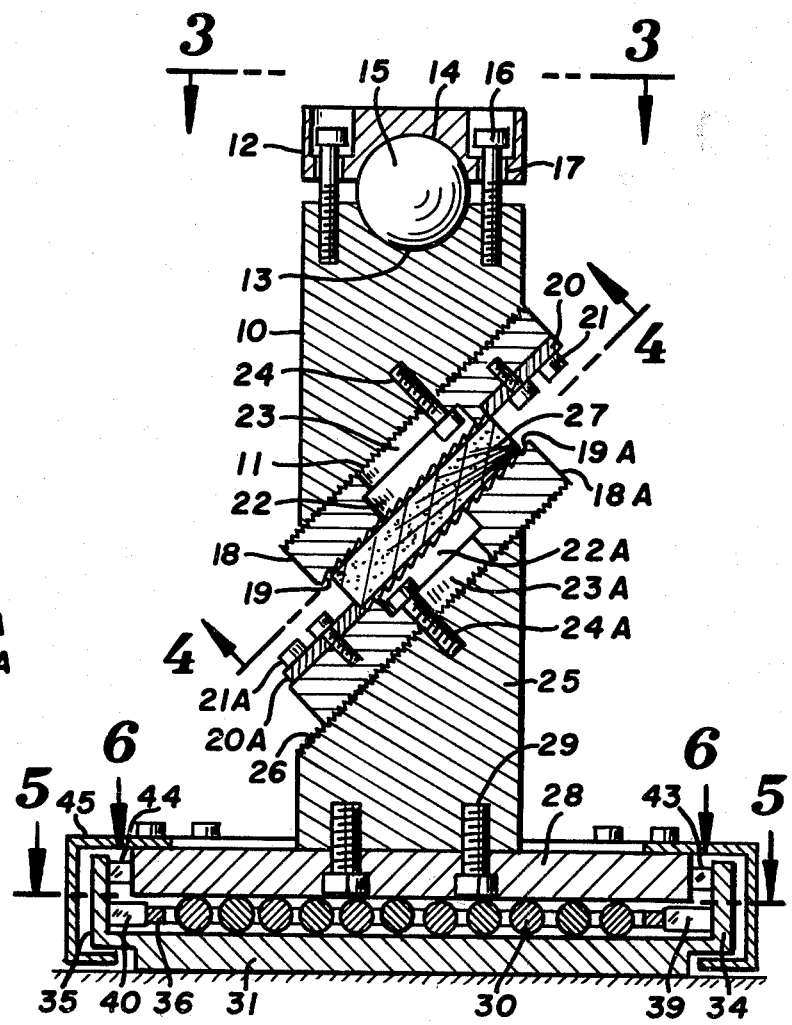
FIG. 2 is a vertical section on the line 2—2 of FIG. 1 and in the direction of the arrows, showing the jig at the point in time immediately prior to application of pressure.
Figure 3:
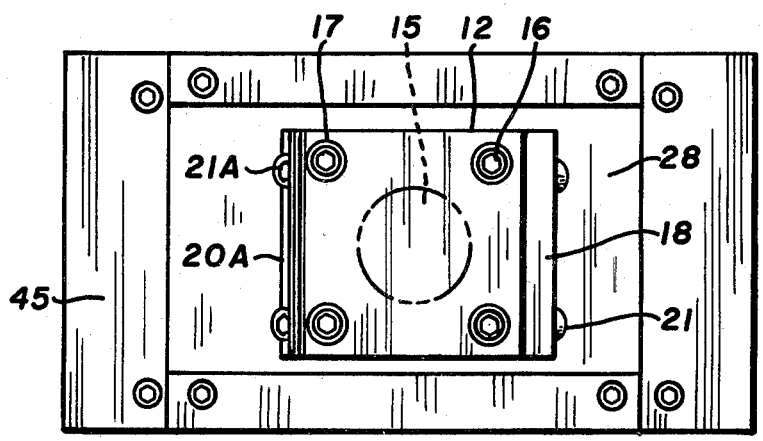
FIG. 3 is a top plan view of the jig.

Referring now to the drawings, and particularly to FIGS. 1 to 3, the compression shear test jig according to the present invention includes an upper loading head having a body 10, having a bottom face 11 formed at substantially a 45° angle. Preferably, the upper loading head also includes a pivotally attached cap 12. The top surface of body 10 and bottom surface of cap 12 are each provided with a truncated hemi-spherical recess or socket, 13 and 14 respectively, adapted to receive and engage a ball 15 which functions as a bearing pivotally supporting the cap.

The cap and ball are held in place by means of screws 16 extending through countersunk oversize holes 17 into the top of the loading head body to loosely sandwich the pivot point between the cap and the upper loading head. The ball transmits the compressive force uniformly to wedge shaped specimens that could result from uneven edge swelling after a water soaking treatment. The ball can be of any strong hard material, such as a 1 inch diameter stainless steel ball bearing. The exact depth the ball is embedded into the cap and upper loading head is arbitrary, but should be deep enough to provide sufficient bearing surface while at the same time leaving a sufficient gap to allow for pivoting. A gap of about 0.125 to 0.250 inches is preferred.

The cap is preferably 2 inches square since this is the common size of samples to be tested. The top face of the upper loading head does not necessarily have to have the same surface dimensions as the cap, but this is preferred. The dimensions could coincide with the dimensions of the test specimen if other than 2 inch specimens were used. Also, the lower part of the loading head could be necked down or expanded to accommodate the specimen.

The jig is intended for use in connection with any universal testing machine, of which there are several (Instron, Baldwin and Tinius-Olson) commercially available. However, any press, preferably fitted with means for measuring force, such as a pressure gauge, may be used. The cap is adapted for easy attachment to and disengagement from the compression means. This may be, for example, by means of slots in the cap engaging a bracket on the press or, preferably by means of a push button activated magnet, such as those sold by L. S. Starrett Company of Athol, Mass. The jig can conveniently be incorporated into a selfcontained desk-top testing apparatus.

Figure 4:
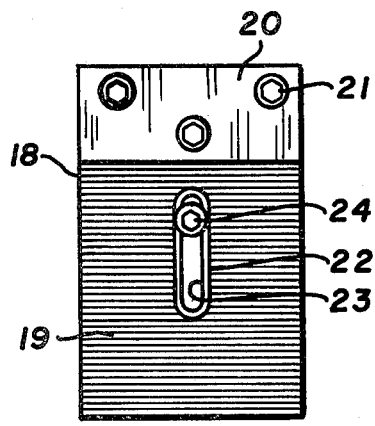
FIG. 4 is a plan view of the upper sample engaging face plate on the line 4—4 of FIG. 2, and in the direction of the arrows.

The 45° miter face 11 of upper loading head body 10 supports a sample engaging face plate 18. (According to the preferred structure plate 18, is separable and adjustable relative to body 10. However, the sample engaging elements about to be described may alternatively be formed directly in face 11.) As best seen in FIG. 4, the outer face of plate 18 is preferably provided with a plurality of parallel horizontal serrations 19 and a horizontal sample restraining bar 20 at its upper end. Aternatively, the face surface may be smooth, or roughened sufficient to grip the test specimen, or knurled, or provided with tooth serrations, or the like, and the retaining element may be projecting pins or the like. The preferred retaining element, bar 20 is desirably separable and secured by means of screws 21. The serrations and restraining bar prevent slippage of the test specimen out of the test jig as the compressive-shear force is transferred.

The face plate is provided with a central longitudinal recess 22 having a central longitudinal slot 23 to permit adjustment of the face plate to accommodate samples of varying thicknesses. The interface between face 11 and face plate 18 is preferably provided with fine horizontal serrations to facilitate accurate adjustment of the face plate, which is then secured by means of one or more screws 24. An important consideration is that the restraining bar and serrations or a reference point must be positioned on the loading face in such a way as to insure accurate positioning of the specimen so that the applied force always is centered through the centroid of the test specimen.

As to the described horizontal serrations, the preferred embodiments are: (1) to have one wall of each serration perpendicular to the loading face and the other wall 45° to it; (2) to have the depth of each serration about 0.015 inches; (3) to have the peaks of the serrations in the same plane as the surface the restraining bar is mounted on; and (4) to have a restraining bar with a thickness of about 0.062 inches or less. The length of the walls of the loading head 10 are arbitrary, but should be long enough to prevent the cap retaining screws 16 from protruding from the loading face 11.

The test jig also includes a lower loading head having a body 25, having a top face 26 formed at substantially a 45° angle. Top face 26 underlies bottom face 11 of upper loading head body 10 and is spaced therefrom and substantially parallel thereto. Face 26 supports sample engaging face plate 18A whose structure is similar to that of face plate 18 already described. This face plate 18A is provided with a plurality of parallel horizontal serrations 19A and a horizontal sample restraining bar 20 at its lower end secured by means of screws 21A. It has a central longitudinal recess 22A and slot 23A and is secured to body 25 by means of screws 24A. The interface between body 25 and face plate 18A at face 26 is provided with fine horizontal serrations. Specimen 27 is placed between the face plates.

The lower loading head is supported by and rigidly secured to a heavy base plate 28, as by means of a plurality of screws 29. The length of the walls of the lower loading head are arbitrary and can be considerably shorter than those of the upper loading head. However, they must be long enough to allow some downward movement of the upper loading head as shear strain develops. The base plate can be an integral unit of the lower loading head, i.e., stamped as one piece or welded, brazed, soldered, riveted or glued together, etc., instead of two separate detachable pieces held together by fasteners, as shown. If the bottom surface of the lower loading head is large the base plate may be omitted.

Figure 5:
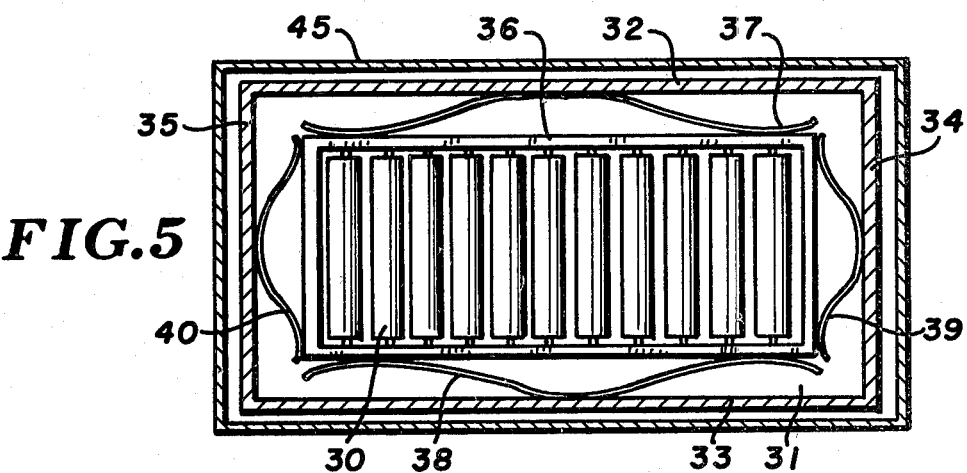
FIG. 5 is a horizontal section on the line 5—5 of FIG. 2 and in the direction of the arrows.

The lower loading head rests on and is supported by a minimum friction surface or device which permits essentially unrestrained lateral movement to occur as shear strain develops. The minimum friction surface may be as simple as a well lubricated surface but preferably, as shown in FIGS. 2 and 5, it is formed by the top edges of a plurality of parallel rollers 30. The rollers are restrained in an oversized box having a bottom 31, side walls 32 and 33, and end walls 34 and 35. The parallel rollers may be loose in the box but preferably are journalled in a yoke or frame 36. That frame in turn is preferably maintained centered by means of leaf springs 37–40 fixed to either the frame or box, or equivalent spring biasing means. Alternatively, a frame of low density plastic foam may be fitted in the space between the roller frame and box walls.

Figure 6:
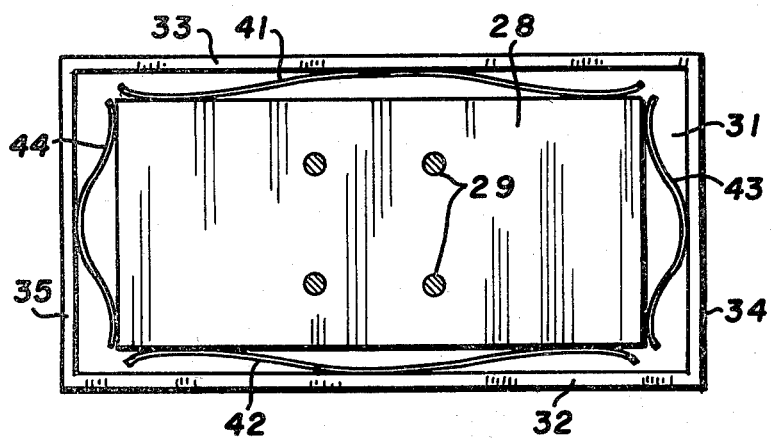
FIG. 6 is a horizontal section on the line 6—6 of FIG. 2 and in the direction of the arrows.

As seen in FIG. 2, the walls 32–35 of the roller retaining box extend higher than the tops of the rollers. As seen in FIG. 6, base plate 28 is also preferably centered, as by spring biasing such as leaf springs 41–44, or a frame of low density plastic foam.

In order to keep dust and other dirt from contaminating the low friction surface system, a shroud or apron 45 is preferably provided. The shroud is supported from the base plate 28. For maximum protection, the bottom box wall 31 is undercut around its periphery and the shroud is provided with an in-turned lip, as shown in FIG. 2.

In use, the jig is placed in a universal testing machine or similar press fitted with a force measuring device. The wood specimen is placed between the sample engaging faces of the loading heads. The face plates are first adjusted for the thickness of the specimen to insure that the applied force is centered through the centroid of the test specimen. The upper loading head transfers pure compressive force from the pivot point to the test specimen as a compressive force perpendicular to the flat face and a shear force parallel to the plane of the flat face. The compressive and shear forces are of equal magnitude and about 71% of the applied force, and the magnitude of the stresses is equal to 17.7% of the applied load. The specimen is tested to shear failure in the weakest plane, and the failing load is recorded.

Two notable differences exist between the test as carried out according to the present invention and the prior art method of Suchsland. No gluing of a test specimen is required. Standard IB sized specimens, 2 inch×2 inch, can be tested directly, without modification. In addition, the pivot point of the described jig allows the load to be applied more uniformly to specimens of non-uniform thickness, and test specimens can strain laterally without restraint. There are further advantages over methods other than Suchsland's. Specimen failure is not limited to a two-dimensional plane. No clamping is required. The jig will accommodate oversize, undersize or out of square specimens. There is one disadvantage, not considered to be significant. The restraining bars cause localized stress concentrations. Combined use of restraining bars and serrations properly designed for the product being tested minimizes this condition.

It is apparent that many modifications and variations of this invention as hereinbefore set forth may be made without departing from the spirit and scope thereof. The specific embodiments described are given by way of example only, and the invention is limited only by the terms of the appended claims.

We claim:

1. A compression shear test jig for determining the internal strength of wood fiberboard and particleboard, said jig comprising:
   (a) an upper loading head including a body having a bottom sample engaging face, said face being disposed at substantially a 45° angle from horizontal, said face having a sample restraining element at its upper end,
   (b) a lower loading head disposed immediately below said upper head and including a body having a top sample engaging face, said face being disposed at substantially a 45° angle from horizontal, spaced from and substantially parallel to the bottom face of the upper head, said top face having a sample restraining element at its lower end, a wood fiberboard or particleboard sample being supportable on the face of the lower head in engagement with the sample restraining element, and the upper head being supportable on the sample, the sample restaining element of the upper head being in engagement with the sample, and
   (c) a horizontal minimum friction surface supporting said lower loading head to permit easy relative horizontal movement of the lower head thereon.

2. A compression shear test jig according to claim 1 wherein said upper loading head includes a cap pivotally secured to the top of said head.

3. A compression shear test jig according to claim 2 wherein:
   (a) the bottom surface of the cap and the top surface of the loading head body each includes a central truncated semi-spherical recess,
   (b) a ball is positioned between the cap and body engaging said recesses, and
   (c) said cap is loosely secured to the body sufficiently to retain said ball and permit relative movement between cap and body.

4. A compression shear test jig according to claim 1 wherein said sample engaging faces are provided with a gripping surface sufficient to securely hold a specimen sample and transfer the shear force from the loading head to the test specimen.

5. A compression shear test jig according to claim 4 wherein said gripping surface is roughened.

6. A compression shear test jig according to claim 5 wherein said roughened gripping surface is serrated.

7. A compression shear test jig according to claim 6 wherein said gripping surface is provided with horizontal serrations.

8. A compression shear test jig according to claim 1 wherein said sample restraining elements are horizontal bars.

9. A compression shear test jig according to claim 1 wherein:
   (a) said lower loading head includes a horizontal base plate rigidly secured to the bottom of the loading head body, and
   (b) the bottom surface of said base plate engages the minimum friction surface.

10. A compression shear test jig according to claim 1 wherein said minimum friction surface is formed by the top edges of a plurality of parallel rollers.

11. A compression shear test jig according to claim 10 wherein:
    (a) said rollers are spaced apart and journalled within a rectangular frame,
    (b) said frame is disposed within an oversized shallow box, the bottom edges of said rollers engaging the top surface of the bottom of the box, and
    (c) spring biasing means between the edges of the roller frame and box walls to flexibly center the frame within the box.

12. A compression shear test jig according to claim 11 wherein:
    (a) said lower loading head includes a horizontal base plate rigidly secured to the bottom of the loading head body,
    (b) said base plate is disposed within said box supported by said rollers,
    (c) spring biasing means between the edges of the base plate and box walls to flexibly center the base plate within the box, and
    (d) a shroud extend from the top of the base plate over and spaced from the outside walls of the box to minimize entry of dirt therein.

13. A compression shear test jig according to claim 1 wherein:
    (a) the sample engaging faces of the upper and lower loading heads are face plates separable from the adjustable relative to the bodies of the loading heads, and
    (b) the interfaces between the face plates and bodies are provided with fine horizontal serrations.

14. A compression shear test jig according to claim 13 wherein:
    (a) each of said face plates is provided with an elongated longitudinal recess in the sample engaging face,
    (b) an elongated longitudinal slot is formed in the bottom of the recess, and
    (c) at least one screw extends from the recess, through the slot and into the head body to adjustably secure the face plate.

15. A compression shear test jig according to claim 8 wherein:
    (a) said sample engaging surfaces are provided with serrations,
    (b) the sample restraining bars are separable from the sample engaging faces of the upper and lower loading heads, (c) said bars are of a thickness to extend about 1/16 inch above the tops of the serrations of the sample engaging faces, and
(d) fastening means extend through the bars into the loading head bodies to rigidly secure the bars.

16. In combination,
(a) press fitted with a force measuring device, and
(b) a compression shear test jig according to claim 1 fitted in said press.

* * * * *